United States Patent

Trah

Patent Number: 5,612,338
Date of Patent: Mar. 18, 1997

[54] PYRAZOLYL ACRYLIC ACID DERIVATIVES, INTERMEDIATES THERETO, AND IN THEIR USE AS MICROBICIDES

[75] Inventor: Stephan Trah, Freiburg, Germany

[73] Assignee: Ciba-Geigy Corporation, Tarrytown, N.Y.

[21] Appl. No.: 495,532

[22] PCT Filed: Jan. 17, 1994

[86] PCT No.: PCT/EP94/00103

§ 371 Date: Jul. 28, 1995

§ 102(e) Date: Jul. 28, 1995

[87] PCT Pub. No.: WO94/17060

PCT Pub. Date: Aug. 4, 1994

[30] Foreign Application Priority Data

Jan. 29, 1993 [CH] Switzerland ............... 292/93

[51] Int. Cl.⁶ ............ A01N 43/66; A01N 43/56; C07D 403/12
[52] U.S. Cl. ............ 514/241; 544/218; 544/219
[58] Field of Search ............ 514/241; 544/218, 544/219

[56] References Cited

U.S. PATENT DOCUMENTS 5,055,477  10/1991  Oda et al. ............ 514/341

OTHER PUBLICATIONS

Patent Abstracts of Japan, 15, No. 271 (C–0848) JP 309 3774 (1991).

Primary Examiner—Patricia L. Morris
Attorney, Agent, or Firm—Edward McC. Roberts

[57] ABSTRACT

Compounds of the formula

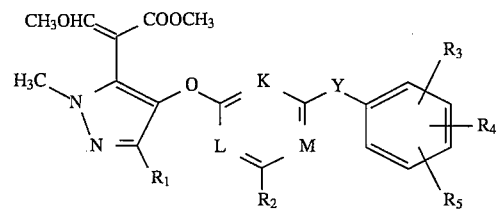

wherein
$R_1$ is hydrogen or methyl,
$R_2$ is hydrogen, halogen, $OCH_3$, $SCH_3$ or CN,
$R_3$, $R_4$, $R_5$ are each independently of one another hydrogen, halogen, $C_1$–$C_4$alkyl, $C_1$–$C_4$alkoxy, $C_2$–$C_5$alkoxycarbonyl, $C_1$–$C_5$alkanoyl, $C_1$–$C_4$haloalkyl, $C_1$–$C_4$haloalkoxy, CN, $NO_2$, or wherein two of those substituents are adjacent to each other and together are a methylenedioxy or difluoromethylenedioxy radical,
K, L, M are each independently of one another CH or N (=nitrogen atom), but at least one of these three substituents is N, and
Y is oxygen or sulfur,
are effective microbicides for controlling fungal diseases. They can be used for plant protection by themselves or as formulated compositions.

6 Claims, No Drawings

PYRAZOLYL ACRYLIC ACID DERIVATIVES, INTERMEDIATES THERETO, AND IN THEIR USE AS MICROBICIDES

The present invention relates to a compound of formula I

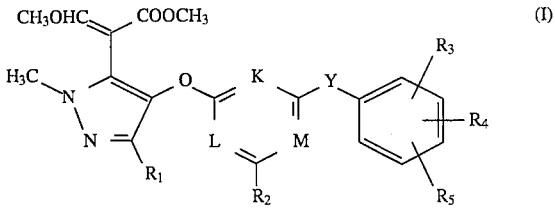

wherein $R_1$ is hydrogen or methyl, $R_2$ is hydrogen, halogen, $OCH_3$, $SCH_3$ or CN, $R_3$, $R_4$, $R_5$ are each independently of one another hydrogen, halogen, $C_1$–$C_4$alkyl, $C_1$–$C_4$alkoxy, $C_2$–$C_5$alkoxycarbonyl, $C_1$–$C_5$alkanoyl, $C_1$–$C_4$haloalkyl, $C_1$–$C_4$haloalkoxy, CN, $NO_2$, or wherein two of these substituents are adjacent to each other and together are a methylenedioxy or difluoromethylenedioxy radical, K, L, M are each independently of one another CH or N (=nitrogen atom), but at least one of these three substituents is N, and Y is oxygen or sulfur.

The compounds of the invention have fungicidal properties and are suitable fungicides especially for use in agriculture and horticulture.

The invention further relates to a process for the preparation of the novel compounds, to fungicidal compositions that contain such compounds as active ingredients, as well as to the use of such compounds and compositions for controlling phytopathogenic fungi.

In the narrower sense, the invention relates to a compound of formula I, wherein $R_1$, $R_2$, K, L, M and Y have the given meanings and $R_3$, $R_4$, $R_5$ are each independently of one another hydrogen, halogen, $C_1C_4$alkyl, $C_1$–$C_4$alkoxy, $C_1$–$C_4$haloalkyl, $C_1$–$C_4$haloalkoxy, CN, $NO_2$, or wherein two of these substituents are adjacent to each other and together are a methylenedioxy or difluoromethylenedioxy radical.

In formula I above and throughout this specification, alkyl, haloalkyl, haloalkoxy or alkoxy groups, depending on the number of carbon atoms, are straight-chain or branched. Alkyl is methyl, ethyl, propyl, isopropyl, butyl, isobutyl, sec-butyl and tert-butyl. The $C_2$–$C_5$alkoxycarbonyl substituent is comprised of a $C_1$–$C_4$alkoxy group and a carbonyl group.

Halogen by itself or as moiety of an alkyl or alkoxy group is fluoro, chloro, bromo or iodo.

If the compounds of formula I contain asymmetrical carbon atoms, then the compounds are obtained in optically active form. Solely owing to the presence of the aliphatic double bond the compounds are obtained at all events in the [E] or [Z] form. Atropisomerism can also occur. All the possible isomeric forms as well as mixtures thereof, for example racemic mixtures and any form of [E/Z] mixtures, are embraced by formula I.

An important group of compounds falling within the scope of formula I embraces those compounds wherein one of the substituents K, L or M is nitrogen and the others are both CH, wherein $R_2$ is hydrogen or halogen, and the substituents $R_1$, $R_3$, $R_4$, $R_5$ and Y have the given meanings (subgroup IA), and, among these, preferably those compounds wherein K is nitrogen, L and M are CH and $R_1$ is methyl (subgroup Ia).

A further important group of compounds falling within the scope of formula I embraces those compounds wherein two of the substituents K, L and M are nitrogen, and the third substituent is CH, and the remaining substituents have the given meanings (subgroup IB) and, among these, preferably those compounds wherein K is CH and L and M are nitrogen, $R_1$ is methyl, $R_4$ is hydrogen and $R_2$, $R_3$, $R_5$ and Y have the given meanings (subgroup IBB).

Within this last mentioned group of pyrimidine derivatives IBB, those compounds are preferred wherein $R_2$ is hydrogen or halogen, Y is oxygen and $R_3$ and $R_5$ are each independently of the other hydrogen, halogen, methyl, ethyl, methoxy, ethoxy, $CF_3$, $OCF_3$, $OCHF_2$, $NO_2$ or CN, or both adjacent to each other are a methylenedioxy or difluoromethylenedioxy radical (subgroup Ib).

A further group of compounds falling within the scope of formula I embraces 1,3,5-triazinyl derivatives, i.e. those compounds wherein the substituents K, L and M are nitrogen, and Y and $R_1$ to $R_5$ have the given meanings (subgroup IC), preferably those compounds wherein $R_1$ is methyl, $R_4$ is hydrogen, Y is oxygen and $R_2$, $R_3$ and $R_5$ have the given meanings (subgroup ICC).

Within this last mentioned group ICC, those compounds are preferred wherein $R_2$ is fluoro, chloro, bromo, $OCH_3$, $SCH_3$ or CN, and $R_3$ and $R_5$ are each independently of the other hydrogen, halogen, methyl, ethyl, methoxy, ethoxy, $CF_3$, $OCF_3$, $OCHF_2$, $NO_2$ or CN, or both adjacent to each other are a methylenedioxy or difluoromethylenedioxy radical (subgroup Ic).

Among the biologically preferred individual compounds of subgroup IBB are the compounds 1.1, 1.3, 1.5, 1.13, 1.28, 1.41, 1.52 and 1.67 listed in Table 1.

The process of this invention for the preparation of the novel compounds of formula I comprises reacting a pyrazolyl acetate derivative of formula V

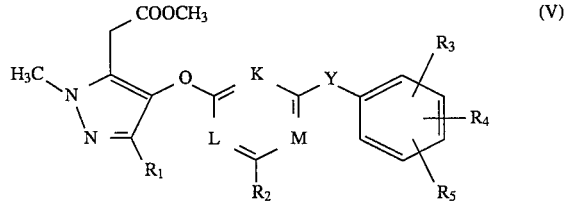

wherein $R_1$ to $R_5$, Y, K, L and M are as defined for formula I in basic medium, with methyl formate, and methylating the 3-hydroxyacrylate so obtained. Suitable methylating reagents include methyl iodide, dimethyl sulfate, diazomethane and the like.

The invention relates likewise to the novel pyrazolyl acetates of formula V, wherein $R_1$ is hydrogen or methyl, $R_2$ is hydrogen, halogen, $OCH_3$, $SCH_3$ or CN, $R_3$, $R_4$, $R_5$ are each independently of one another hydrogen, halogen, $C_1$–$C_4$alkyl, $C_1$–$C_4$alkoxy, $C_2$–$C_5$alkoxycarbonyl, $C_1$–$C_5$alkanoyl, $C_1$–$C_4$haloalkyl, $C_1$–$C_4$haloalkoxy, CN, $NO_2$, or wherein two of these substituents are adjacent to each other and together are a methylenedioxy or difluoromethylenedioxy radical, K, L, M are each independently of one another CH or N, but at least one of the three substituents is N, and Y is oxygen or sulfur;

as well as to a process for the preparation of said compounds of formula V, which comprises reacting a (4-hydroxypyrazol-5-yl)methyl acetate derivative of formula III

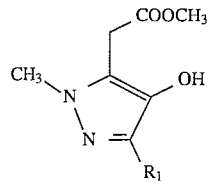 (III)

wherein $R_1$ is hydrogen or methyl, either a) with a heterocyclylphenyl(thio)ether of formula VII

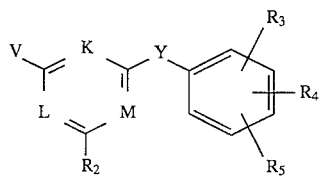 (VII)

or b) initially with a heterocyclic compound of formula VIII

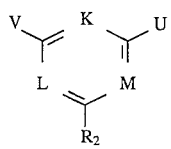 (VIII)

to give an intermediate of formula IV

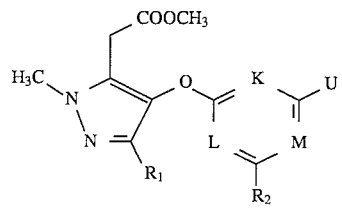 (IV)

and reacting said intermediate with a (thio)phenol derivative of formula IX

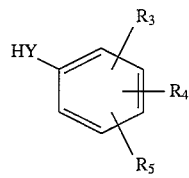 (IX)

in which formulae VII, VIII, IV and IX above the substituents $R_1$ to $R_5$, Y, K, L and M are as defined for formula V, while U and V in formulae IV, VII and VIII are a leaving group, preferably chloro, bromo, iodo, mesyloxy, benzenesulfonyloxy or tosyloxy.

Both process steps a) and b) can be carried out in inert solvents, conveniently in the presence of a base. The reaction temperature is in the range from −20° C. to the boiling temperature of the solvent, the preferred range being from 0° C. to 150° C.

Illustrative examples of suitable inert solvents are: aliphatic and aromatic unsubstituted or halogenated hydrocarbons such as pentane, hexane, heptane, cyclohexane, petroleum ether, petroleum spirit, ligroin, benzene, toluene, methylene chloride, ethylene chloride, chloroform, carbon tetrachloride, chlorobenzene, o-dichlorobenzene; also ethers, including diethyl and dibutyl ether, glycol dimethyl ether and diglycol dimethyl ether, tetrahydrofuran and dioxane; ketones, typically acetone, methyl ethyl ketone, methyl isopropyl ketone and methyl isobutyl ketone; nitriles, including acetonitrile and propionitrile, benzonitrile, glutarodinitrile; amides, typically dimethyl formamide, dimethyl acetamide and N-methylpyrrolidone; as well as dimethyl surfoxide, tetramethylensulfone and hexamethylphosphoric triamide. It is also possible to use mixtures of the aforementioned solvents.

Suitable bases typically include: hydroxides, hydrogencarbonates, carbonates and alcoholates of alkali metals and alkaline earth metals (Li, Na, K, Ca, Mg), sodium hydride, tertiary amines such as trimethylamine, triethylamine, pyridine, picolines, N-methylmorpholine, N-ethylpyrrolidine, diazabicyclo(4,3,0)undecane (DBU), 1,4-diazabicyclo-2,2,2-octane (DABCO), diazabicyclo(3,2,0)nonane (DBN).

Silver oxide may also be used as weakly catalytic base.

The novel compounds of formula I can be prepared in accordance with the following synthesis scheme 1:

Synthesis scheme 1:

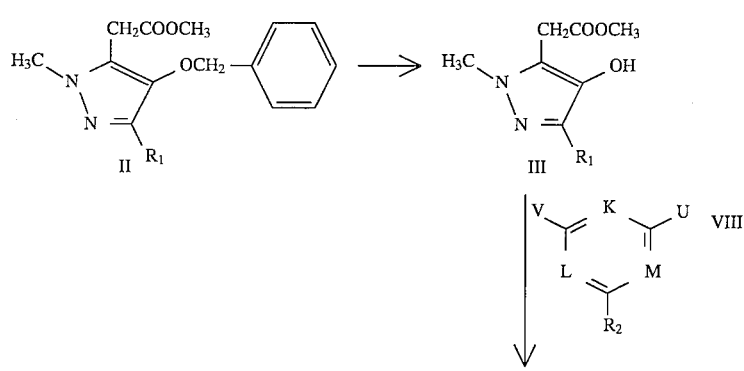

-continued
Synthesis scheme 1:

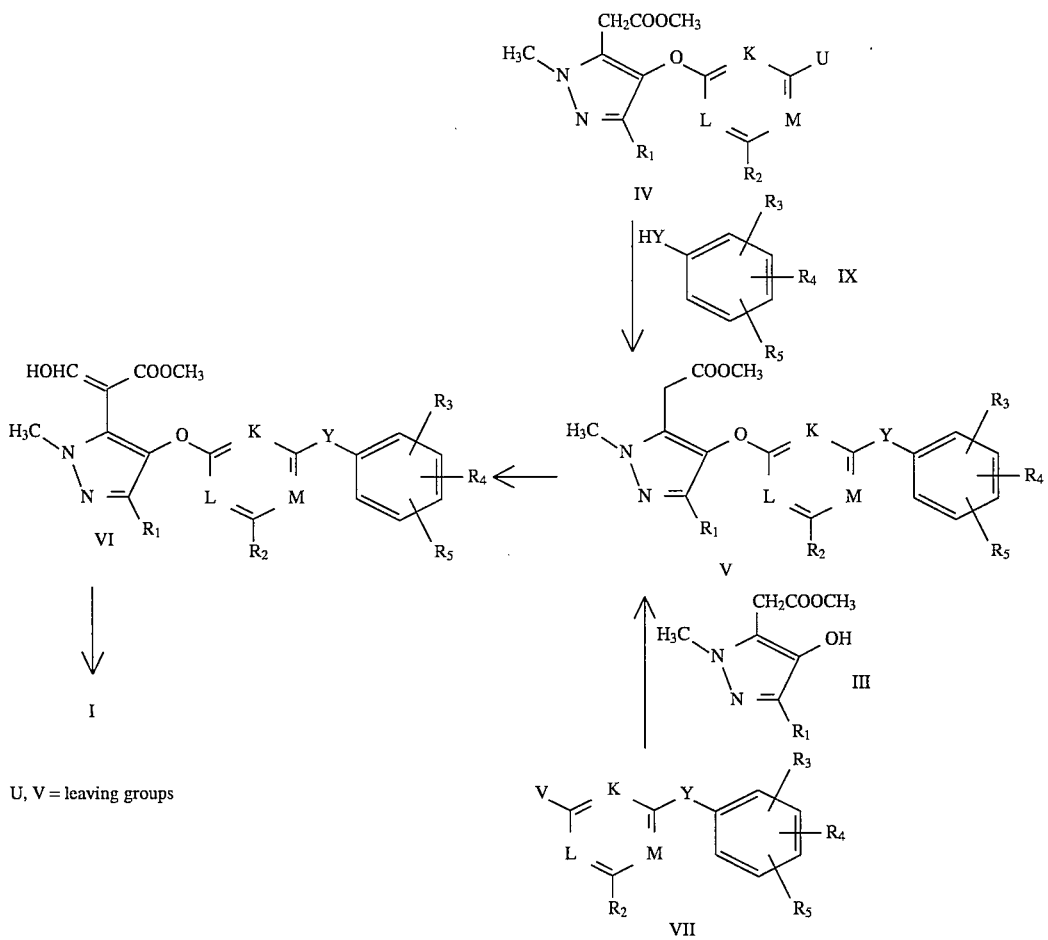

U, V = leaving groups

The compounds of formula I so obtained can be isolated and purified by methods that are known per se. Mixtures of isomers, for example mixtures of E/Z isomers, can likewise be separated by per se known methods into the pure isomers, typically by chromatography or fractional crystallisation.

The 4-hydroxypyrazolylmethyl acetate of formula III can be obtained by the method disclosed in EP-A-483 851 by hydrogenation of the corresponding 4-benzyl ether. This 4-benzyl ether can be obtained by the method disclosed in EP-A-433 899 (for the preparation of the starting materials of "formula IIb" as defined therein).

Illustrative examples of solvents which may suitably be used for this hydrogenation are hydrocarbons such as toluene, benzene, xylene, petroleum ether etc.; esters such as ethyl acetate etc.; carboxylic acids such as glacial acetic acid, formic acid etc.; alcohols such as methanol, ethanol, glycol etc.; ethers such as diethyl ether, dioxane, tetrahydrofuran etc. The presence of palladium/carbon as catalyst for speeding up the reaction is advantageous. The reaction temperature is in the range from 0° C. to the boiling temperature of the solvent, preferably in the range from room temperature to 70° C.

Compounds of formula I can also be prepared by a process analogous to that of synthesis scheme 1, wherein the acetate radical in formula II is present from the start in the methoxyacrylate radical (EP-A1-433 899, page 6 et seq.).

The invention also relates to the novel intermediate of formula III

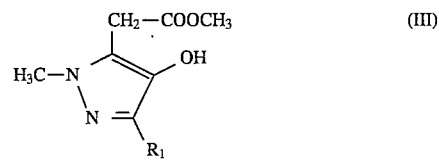

wherein $R_1$ is hydrogen or methyl.

It has been found that the compounds of formula I have, for practical purposes, a particularly advantageous microbicidal spectrum for controlling phytopathogenic micro-organisms, especially fungi. They have very useful curative, preventive and, in particular, systemic properties, and are used for protecting numerous cultivated plants. The compounds of formula I can be used to inhibit or destroy the pests which occur on plants or parts of plants (fruit, blossoms, leaves, stems, tubers, roots) in different crops of useful plants, while at the same time the parts of plants which grow later are also protected from attack by phytopathogenic microorganisms.

The compounds of formula I can also be used as dressing agents for protecting seeds (fruit, tubers, grains) and plant cuttings against fungal infections as well as against phytopathogenic fungi which occur in the soil.

The compounds of formula I are effective against the phytopathogenic fungi belonging to the following classes: Fungi imperfecti (in particular Botrytis and also Pyricularia, Helminthosporium, Fusarium, Septoria, Cercospora, Cercosporella and Alternaria); Basidiomycetes (e.g. Rhizocotonia, Hemileia, Puccinia). They are also effective against the class of the Ascomycetes (e.g. Venturia and Erysiphe, Podosphaera, Monilinia and Uncinula), and especially against that of the Oomycetes (e.g. Phytophthora, Peronospora, Bremia, Pythium, Plasmopara).

Target crops suitable for the plant protective utility disclosed herein typically comprise within the scope of the present invention the following species of plants: cereals (wheat, barley, rye, oats, rice, maize, sorghum and related species), beet (sugar beet and fodder beet), pomes, drupes and soft fruit (apples, pears, plums, peaches, almonds, cherries, strawberries, gooseberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, sweet peppers), lauraceae (avocados, cinnamon, camphor), or plants such as tobacco, nuts, coffee, sugar cane, tea, pepper, vines, hops, egg-plants, bananas and natural rubber plants, as well as ornamentals.

The compounds of formula I are usually applied in the form of compositions and can be applied to the crop area or plant to be treated, simultaneously or in succession, with further compounds. These further compounds can be fertilisers or micronutrient donors as well as other other preparations that influence plant growth. It is also possible in this connection to use selective herbicides, insecticides, fungicides, bactericides, nematicides, mollusicides or mixtures of several of these preparations, together with optional carriers, surfactants or application-promoting adjuvants commonly employed in the art of formulation.

Suitable carriers and adjuvants may be solid or liquid and correspond to the appropriate substances ordinarily employed in formulation technology, including natural or regenerated mineral substances, solvents, dispersants, wetting agents, tackifiers, thickeners, binders or fertilisers.

Suitable solvents are: aromatic hydrocarbons, the fractions containing 8 to 12 carbon atoms, typically xylene mixtures or substituted naphthalenes, phthalates such as dibutyl or dioctyl phthalate, aliphatic hydrocarbons such as cyclohexane or paraffins; also alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers typically used for dusts and dispersible powders are usually natural mineral fillers such as calcite, talcum, kaolin, montmorillonite or attapulgite.

Further especially useful application-promoting adjuvants that may lead to a reduction of the concentration of active ingredient are natural (animal or vegetable) or synthetic phospholipids of the series of the cephalins and lecithins which can conveniently be isolated from soybeans.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be water-soluble soaps as well as water-soluble synthetic surface-active compounds.

Suitable soaps are the alkali metal salts, alkaline earth metal salts or ammonium salts or substituted ammonium salts of higher fatty acids ($C_{10}$–$C_{22}$), typically the sodium or potassium salts of oleic or stearic acid, or of natural fatty acid mixtures which can be obtained, inter alia, from coconut oil or tallow oil. Further suitable surfactants are also the fatty acid methyltaurin salts.

Nonionic surfactants are polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Typical examples of nonionic surfactants are nonylphenolpolyethoxyethanols, castor oil polyglycol ethers, adducts of polypropylene and polyethylene oxide, tributylphenoxypolyethhoxyethanol, polyethylene glycol and octylphenoxypolyethoxyethanol.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituents, at least one $C_8$–$C_{22}$alkyl radical and, as further substituents, optionally halogenated lower alkyl, benzyl or hydroxy-lower alkyl radicals.

The anionic, nonionic or cationic surfactants customarily employed in formulation technology are familiar to those skilled in the an or may be found in the relevant literature.

"Mc Cutcheon's Detergents and Emulsifiers Annual", Mc Publishing Corp., Glen Rock, N.J., 1988.

M. and J. Ash, "Encyclopedia of Surfactants", Vol. I–III, Chemical Publishing Co., New York, 1980–1981.

Dr. Helmut Stache "Tensid-Taschenbuch" (Handbook of Surfactants), Carl Hanser Verlag, Munich/Vienna 1981.

The agrochemical compositions usually contain 0.1 to 99% by weight, preferably 0.1 to 95% by weight, of a compound of formula I, 99.9 to 1% by weight, preferably 99.9 to 5% by weight of a solid or liquid adjuvant, and 0 to 25% by weight, preferably 0.1 to 25% by weight, of a surfactant.

Whereas commercial products will preferably be formulated as concentrates, the end user will normally use formulations diluted to concentrations down to 0.0001%.

The compositions may also contain further ingredients such as stabilisers, antifoams, viscosity regulators, binders, tackifiers as well as fertilisers or other chemical agents to obtain special effects.

The formulations, i.e. the compositions, preparations or mixtures containing the compound of formula I and, where appropriate, a solid or liquid adjuvant, are prepared in known manner, conveniently by homogeneously mixing and/or grinding the active ingredient with extenders, as with a solvent (mixture), a solid carrier and, in some cases, surface-active compounds (surfactants).

A preferred method of applying a compound of formula I, or an agrochemical composition which contains at least one of said compounds, is foliar application. The frequency of application and the rate of application will depend on the risk of infestation by the corresponding pathogen. However, the compound of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds either with a liquid formulation of the fungicide or coating them with a solid formulation. In principle, any kind of plant propagation material can be protected with compounds of formula I, e.g. seeds, roots or stems.

The compounds of formula I are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations in polymeric substances. As with the type of the compositions, the methods of application, such as spraying, atomising, dusting, scattering, coating or pouring, are chosen in accordance with the intended objectives and the prevailing circumstances. Advantageous rates of application are normally from 10 g to 2 kg of active ingredient (a.i.) per hectare, preferably from 25 g to 800 g a.i./ha. For use as seed dressing agents, advantageous rates of application are from 0.001 g to 1.0 g active ingredient per kg of seeds.

The invention is illustrated in more detail by the following non-limitative Examples.

EXAMPLE P1 a) Preparation of the intermediate of formula III
Methyl (1,3-dimethyl-4-hydroxypyrazol-5-yl)acetate:

A solution of 10.3 g (37.5 mmol) of methyl (4-benzyloxy-1,3-dimethylpyrazol-5-yl)acetate in 200 ml of methanol is hydrogenated in the presence of 1 g of 10% Pd/C. When the reaction is complete, the reaction mixture is filtered and the filtrate is concentrated under vacuum. The residue is recrystallised from dichloromethane/n-hexane, giving methyl (1,3-dimethyl-4-hydroxypyrazol-5-yl)acetate; m.p. 119°–120° C.

b) Preparation of the intermediate of formula V
Methyl {1,3-dimethyl-4-[6-(2-fluorophenoxy)pyrimidin-4-yloxy]pyrazol-5-yl}acetate:

To a solution of 3.0 g (16.3 mmol) of methyl (1,3-dimethyl-4-hydroxypyrazol-5-yl)acetate in 80 ml of dimethyl formamide are added 6.9 g (50.0 mmol) of potassium carbonate and 2.7 g (18.0 mmol) of 4,6-dichloropyrimidine. After stirring for 3 hours at room temperature, 2.2 g (20.0 mmol) of 2-fluorophenol are added and stirring is continued for 3 hours at 80°–85° C. Then 300 ml of ice-water are added, followed by extraction with 400 ml of diethyl ether. The organic phase is washed with 2M sodium hydroxide solution, water and sodium chloride solution, dried and concentrated under vacuum. The resultant brown oil is chromatographed over silica gel with tetrahydrofuran/n-hexane (1:1) as eluant, giving methyl {1,3-dimethyl-4-[6-(2-fluorophenoxy)pyrimidin-4-yloxy]pyrazol-5-yl}acetate as a yellow resin: MS: 372 ($M^+$, 80%), 312 (100).

c) Preparation of the final product
E-Methyl-2-{1,3-dimethyl-4-[6-(2-fluorophenoxy)-pyrimidin-4-yloxy]pyrazol-5-yl}-3-methoxyacrylate (compound 1.3, Table 1):

A solution of 3.5 g (9.3 mmol) of methyl {1,3-dimethyl-4-[6-(2-fluorophenoxy)pyrimidin-4-yloxy]pyrazol-5-yl}acetate and 10 ml of methyl formate in 10 ml of dimethyl formamide is slowly added dropwise to a suspension of 0.5 g (20.0 mmol) of sodium hydride (95%) in 40 ml of dimethyl formamide, while keeping the temperature below 30° C. The reaction mixture is stirred for 2 hours at room temperature, acidified with acetic acid and, after addition of 200 ml of ice-water, extracted with 200 ml of ethyl acetate. The organic phase is washed with water and sodium chloride solution, dried and concentrated under vacuum, giving E-methyl-2-{1,3-dimethyl-4-[6-(2-fluorophenoxy)pyrimidin-4-yloxy]pyrazol-5-yl}-3-hydroxyacrylate as a brown resin, which is stirred together with 1.8 g (13.0 mmol) of potassium carbonate and 0.9 ml (6.7 mmol) of dimethyl sulfate in 40 ml of acetone for 3 hours at room temperature. The reaction mixture is filtered, the filtrate is diluted with 50 ml of water and extracted with 100 ml of ethyl acetate. The organic phase is washed with sodium chloride solution, dried and concentrated under vacuum. The residue is chromatographed over silica gel tetrahydrofuran/n-hexane (1:1) as eluant, giving E-methyl-2-{1,3-dimethyl-4-[6-(2-fluorophenoxy)pyrimidin-4-yloxy]pyrazol-5-yl}-3-methoxyacrylate as a yellow resin; MS: 414 ($M^+$, 44%), 75 (100).

The following compounds can be prepared in this manner or according to one of the above described methods.

TABLE 1

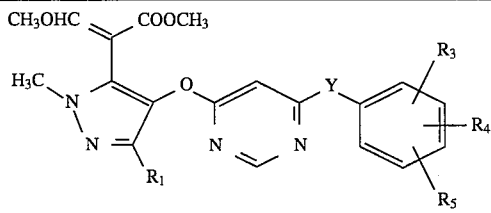

| Cmpd. | $R_1$ | Y | $R_3$ | $R_4$ | $R_5$ | Phys. data |
|---|---|---|---|---|---|---|
| 1.1 | $CH_3$ | O | 2-CN | H | H | mp. 114–116° C. |
| 1.2 | $CH_3$ | O | H | H | H | |
| 1.3 | $CH_3$ | O | 2-F | H | H | MS: 414($M^+$, 44%), 75 (100) |
| 1.4 | $CH_3$ | O | 2-Cl | H | H | MS: 430($M^+$, 39%), 75 (100) |
| 1.5 | $CH_3$ | O | 2-Br | H | H | MS: 474($M^+$, 31%), 75 (100) |
| 1.6 | $CH_3$ | O | 2-Me | H | H | MS: 410($M^+$, 31%), 75 (100) |
| 1.7 | $CH_3$ | O | 2-OMe | H | H | MS: 426($M^+$, 53%), 395 (100) |
| 1.8 | $CH_3$ | O | 2-$CF_3$ | H | H | |
| 1.9 | $CH_3$ | O | 2-$NO_2$ | H | H | mp. 143–145° C. |
| 1.10 | $CH_3$ | O | 3-CN | H | H | mp. 143–145° C. |
| 1.11 | $CH_3$ | O | 3-F | H | H | MS: 414($M^+$, 83%), 75 (100) |
| 1.12 | $CH_3$ | O | 3-Cl | H | H | MS: 430($M^+$, 44%), 75 (100) |
| 1.13 | $CH_3$ | O | 3-Br | H | H | MS: 474($M^+$, 27%), 75 (100) |
| 1.14 | $CH_3$ | O | 3-Me | H | H | MS: 410($M^+$, 79%), 75 (100) |
| 1.15 | $CH_3$ | O | 3-OMe | H | H | MS: 426($M^+$, 53%), 75 (100) |
| 1.16 | $CH_3$ | O | 3-$CF_3$ | H | H | MS: 464($M^+$, 74%), 75 (100) |
| 1.17 | $CH_3$ | O | 3-$OCF_3$ | H | H | |

TABLE 1-continued

| Cmpd. | R₁ | Y | R₃ | R₄ | R₅ | Phys. data |
|---|---|---|---|---|---|---|
| 1.18 | CH₃ | O | 3-NO₂ | H | H | m.p. 173–175° C. |
| 1.19 | CH₃ | O | 4-CN | H | H | |
| 1.20 | CH₃ | O | 4-F | H | H | MS: 414(M⁺, 57%), 75 (100) |
| 1.21 | CH₃ | O | 4-Cl | H | H | MS: 430(M⁺, 42%), 75 (100) |
| 1.22 | CH₃ | O | 4-Br | H | H | MS: 474(M⁺, 38%), 75 (100) |
| 1.23 | CH₃ | O | 4-Me | H | H | MS: 410(M⁺, 81%), 75 (100) |
| 1.24 | CH₃ | O | 4-OMe | H | H | |
| 1.25 | CH₃ | O | 4-CF₃ | H | H | |
| 1.26 | CH₃ | O | 4-OCF₃ | H | H | |
| 1.27 | CH₃ | O | 4-NO₂ | H | H | |
| 1.28 | CH₃ | O | 2-Et | H | H | MS: 424(M⁺, 100%), 75 (72) |
| 1.29 | CH₃ | O | 2-OEt | H | H | |
| 1.30 | CH₃ | O | 3,4-methylenedioxy | | H | MS: 440(M⁺, 100%), 75 (82) |
| 1.31 | CH₃ | O | 2-F | 3-F | H | |
| 1.32 | CH₃ | O | 2-Cl | 3-Cl | H | |
| 1.33 | CH₃ | O | 2-Me | 3-Me | H | MS: 424(M⁺, 42%), 75 (100) |
| 1.34 | CH₃ | O | 2-OMe | 3-OMe | H | |
| 1.35 | CH₃ | O | 3-F | 5-F | H | |
| 1.36 | CH₃ | O | 3-Cl | 5-Cl | H | |
| 1.37 | CH₃ | O | 3-Me | 5-Me | H | MS: 424(M⁺, 90%), 75 (100) |
| 1.38 | CH₃ | O | 3-OMe | 5-OMe | H | |
| 1.39 | CH₃ | O | 2-F | 4-F | H | |
| 1.40 | CH₃ | O | 2-Me | 4-Me | H | MS: 424(M⁺, 74%), 75 (100) |
| 1.41 | CH₃ | O | 2-Me | 4-Cl | H | MS: 444(M⁺, 58%), 75 (100) |
| 1.42 | CH₃ | O | 3-OMe | 4-OMe | 5-OMe | |
| 1.43 | H | O | 2-CN | H | H | |
| 1.44 | H | O | H | H | H | |
| 1.45 | H | O | 2-F | H | H | |
| 1.46 | H | O | 2-Cl | H | H | |
| 1.47 | H | O | 2-Br | H | H | |
| 1.48 | H | O | 2-Me | H | H | |
| 1.49 | H | O | 2-OMe | H | H | |
| 1.50 | H | O | 2-CF₃ | H | H | |
| 1.51 | H | O | 2-NO₂ | H | H | |
| 1.52 | CH₃ | S | H | H | H | MS: 412(M⁺, 64%), 75 (100) |
| 1.53 | CH₃ | S | 2-Cl | H | H | m.p. 138–140° C. |
| 1.54 | CH₃ | S | 2-Br | H | H | |
| 1.55 | CH₃ | S | 2-Me | H | H | |
| 1.56 | CH₃ | S | 2-OMe | H | H | m.p. 162–164° C. |
| 1.57 | CH₃ | O | 3,4-difluoromethyl-enedioxy | | H | |
| 1.58 | CH₃ | O | 3-Et | H | H | MS: 424(M⁺, 58%), 75 (100) |
| 1.59 | CH₃ | O | 2-Cl | 5-Me | H | m.p. 161–163° C. |
| 1.60 | CH₃ | O | 3-Cl | 4-F | H | m.p. 122–124° C. |
| 1.61 | CH₃ | O | 3-Me | 4-Cl | 5-Me | MS: 458(M⁺, 52%), 75 (100) |
| 1.62 | CH₃ | O | 4-Et | H | H | MS: 424(M⁺, 100%), 75 (38) |
| 1.63 | CH₃ | O | 3-Me | 4-Cl | H | MS: 444(M⁺, 71%), 75 (100) |
| 1.64 | CH₃ | O | 3-Me | 4-Me | H | MS: 424(M⁺, 60%), 75 (100) |
| 1.65 | CH₃ | O | 2-COOMe | H | H | MS: 454(M⁺, 62%), 75 (100) |
| 1.66 | CH₃ | O | 2-CHO | H | H | m.p. 111–115° C. |
| 1.67 | CH₃ | O | 2-COMe | H | H | MS: 438(M⁺, 100%), 75 (75) |

TABLE 2

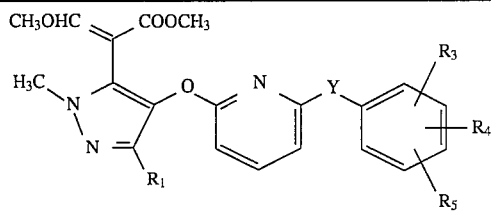

| Cmpd. | R₁ | Y | R₃ | R₄ | R₅ | Phys. data |
|---|---|---|---|---|---|---|
| 2.1 | CH₃ | O | 2-CN | H | H | |
| 2.2 | CH₃ | O | H | H | H | |
| 2.3 | CH₃ | O | 2-F | H | H | |
| 2.4 | CH₃ | O | 2-Cl | H | H | |
| 2.5 | CH₃ | O | 2-Br | H | H | |
| 2.6 | CH₃ | O | 2-Me | H | H | |
| 2.7 | CH₃ | O | 2-OMe | H | H | |
| 2.8 | CH₃ | O | 2-CF₃ | H | H | |
| 2.9 | CH₃ | O | 2-NO₂ | H | H | |
| 2.10 | H | O | 2-CN | H | H | |
| 2.11 | H | O | H | H | H | |
| 2.12 | H | O | 2-F | H | H | |
| 2.13 | H | O | 2-Cl | H | H | |
| 2.14 | H | O | 2-Br | H | H | |
| 2.15 | H | O | 2-Me | H | H | |

TABLE 2-continued

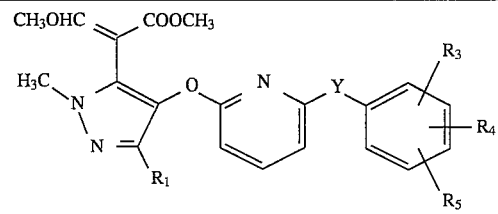

| Cmpd. | R₁ | Y | R₃ | R₄ | R₅ | Phys. data |
|---|---|---|---|---|---|---|
| 2.16 | H | O | 2-OMe | H | H | |
| 2.17 | H | O | 2-CF₃ | H | H | |
| 2.18 | H | O | 2-NO₂ | H | H | |
| 2.19 | CH₃ | S | H | H | H | |
| 2.20 | CH₃ | S | 2-Cl | H | H | |
| 2.21 | CH₃ | S | 2-Br | H | H | |
| 2.22 | CH₃ | S | 2-Me | H | H | |
| 2.23 | CH₃ | S | 2-OMe | H | H | |
| 2.24 | CH₃ | O | 4-Cl | H | H | oil |
| 2.25 | CH₃ | O | 4-NO₂ | H | H | |
| 2.26 | CH₃ | O | 3-Me | H | H | oil |
| 2.27 | CH₃ | O | 3,4-difluoromethyl-enedioxy | | H | |

TABLE 3

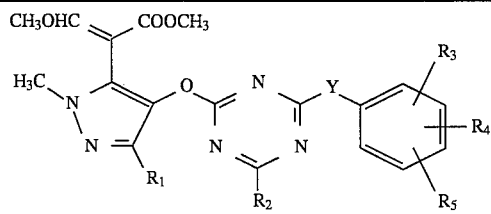

| Cmpd. | R₁ | R₂ | Y | R₃ | R₄ | R₅ | Phys. data |
|---|---|---|---|---|---|---|---|
| 3.1 | CH₃ | Cl | O | 2-CN | H | H | MS: 456(M⁺, 16%), 75 (100) |
| 3.2 | CH₃ | Cl | O | H | H | H | |
| 3.3 | CH₃ | Cl | O | 2-F | H | H | |
| 3.4 | CH₃ | Cl | O | 2-Cl | H | H | |
| 3.5 | CH₃ | Cl | O | 2-Br | H | H | |
| 3.6 | CH₃ | Cl | O | 2-Me | H | H | |
| 3.7 | CH₃ | Cl | O | 2-OMe | H | H | |
| 3.8 | CH₃ | Cl | O | 2-CF₃ | H | H | |
| 3.9 | CH₃ | Cl | O | 2-NO₂ | H | H | |
| 3.10 | H | Cl | O | 2-CN | H | H | |
| 3.11 | H | Cl | O | H | H | H | |
| 3.12 | CH₃ | Cl | S | H | H | H | |
| 3.13 | CH₃ | OMe | O | 2-CN | H | H | |
| 3.14 | CH₃ | OMe | O | H | H | H | |
| 3.15 | CH₃ | OMe | S | H | H | H | |
| 3.16 | CH₃ | SMe | O | 2-CN | H | H | |
| 3.17 | CH₃ | SMe | O | H | H | H | |
| 3.18 | CH₃ | SMe | S | H | H | H | |
| 3.19 | CH₃ | CN | O | 2-CN | H | H | |
| 3.20 | CH₃ | CN | O | H | H | H | |
| 3.21 | CH₃ | CN | S | H | H | H | |
| 3.22 | CH₃ | H | O | 2-CN | H | H | |
| 3.23 | CH₃ | H | O | H | H | H | |
| 3.24 | CH₃ | H | S | H | H | H | |
| 3.25 | CH₃ | H | O | 4-Cl | H | H | |
| 3.26 | CH₃ | H | O | 4-NO₂ | H | H | |
| 3.27 | CH₃ | H | O | 3-Me | H | H | |
| 3.28 | CH₃ | H | O | 4-Me | H | H | |
| 3.29 | CH₃ | H | O | 3,4-difluoro-methylenedioxy | | H | |

2. Formulation Examples for compounds of formula I
(%=percentage by weight)

| 2.1. Emulsifiable concentrates | a) | b) | c) |
|---|---|---|---|
| compound of Tables 1–3 | 25% | 40% | 50% |
| calcium dodecylbenzenesulfonate | 5% | 8% | 6% |
| castor oil polyethylene glycol ether (36 mol ethylene oxide) | 5% | — | — |
| tributylphenyl polyethylene glycol ether % (30 mol ethylene oxide) | — | 12% | 4 |
| cyclohexanone | — | 15% | 20% |
| xylene mixture | 65% | 25% | 20% |

Emulsions of any desired concentration can be prepared by diluting such concentrates with water.

| 2.2. Solutions | a) | b) | c) | d) |
|---|---|---|---|---|
| compound of Tables 1–3 | 80% | 10% | 5% | 95% |
| ethylene glycol monomethyl ether | 20% | — | — | — |
| polyethylene glycol 400 | — | 70% | — | — |
| N-methyl-2-pyrrolidone | — | 20% | — | — |
| epoxidised coconut oil | — | — | 1% | 5% |
| petroleum distillate boiling range: 160–190° C.) | — | — | 94% | — |

These solutions are suitable for application in the form of microdrops.

| 2.3. Granulates | a) | b) |
|---|---|---|
| compound of Tables 1–3 | 5% | 10% |
| kaolin | 94% | — |
| highly disperse silica | 1% | — |
| attapulgite | — | 90% |

The compound is dissolved in methylene chloride, the solution is sprayed on to the carrier and the solvent is then evaporated under vacuum.

| 2.4. Dusts | a) | b) |
|---|---|---|
| compound of Tables 1–3 | 2% | 5% |
| highly disperse silica | 1% | 5% |
| talcum | 97% | — |
| kaolin | — | 90% |

Ready-for-use dusts are obtained by intimately the carriers with the compound.

| 2.5. Wettable powders | a) | b) | c) |
|---|---|---|---|
| compound of Tables 1–3 | 25% | 50% | 75% |
| sodium ligninsulfonate | 5% | 5% | — |
| sodium lauryl sulfate | 3% | — | 5% |
| sodium diisobutylnaphthalene sulfonate | — | 6% | 10% |
| octylphenol polyethylene glycol ether (7–8 mol ethylene oxide) | — | 2% | — |
| highly dispersed silica | 5% | 10% | 10% |
| kaolin | 62% | 27% | — |

The compound is thoroughly mixed with the adjuvants and the mixture is well ground in a suitable mill to give wettable powders which can be diluted with water to suspensions of any desired concentration.

| 2.6 Emulsifiable concentrate | |
|---|---|
| compound of Tables 1–3 | 10% |
| octylphenol polyethylene glycol ether (4–5 mol ethylene oxide) | 3% |
| calcium dodecylbenzenesulfonate | 3% |
| castor oil polyglycol ether (35 mol ethylene oxide) | 4% |
| cyclohexanone | 34% |
| xylene mixture | 50% |

Emulsions of any desired concentration can be prepared by diluting this concentrate with water.

| 2.7. Dusts | a) | b) |
|---|---|---|
| compound of Tables 1–3 | 5% | 8% |
| talcum | 95% | — |
| kaolin | — | 92% |

Ready-for-use dusts are obtained by grinding the active ingredient with the carrier in a suitable mill.

| 2.8 Extruder granulate | |
|---|---|
| compound of Tables 1–3 | 10% |
| sodium ligninsulfonate | 2% |
| carboxymethyl cellulose | 1% |
| kaolin | 87% |

The active ingredient is mixed with the adjuvants, the mixture is ground and moistened with water. This mixture is extruded and then dried in a stream of air.

| 2.9 Coated granulate | |
|---|---|
| compound of Tables 1–3 | 3% |
| polyethylene glycol 200) | 3% |
| kaolin | 94% |

The finely ground compound is applied uniformly in a mixer to the kaolin which is moistened with polyethylene glycol to give non-dusting coated granulates.

| 2.10 Suspension concentrate | |
|---|---|
| compound of Table 1 | 40% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous solution of formaldehyde | 0.2% |
| silicone oil in the form of a 75% aqueous emulsion | 0.8% |
| water | 32% |

The finely ground compound is intimately mixed with the adjuvants to give a suspension concentrate from which suspensions of any desired concentration can be prepared by dilution with water.

Biological Examples

In the following Examples B1 to B13, the compounds of the invention are very effective against fungal attack.

Example B1

Action against *Phytophthora infestans* on tomatoes
a) Curative action

After a cultivation period of 3 weeks, tomato plants of the "Roter Gnom" variety are sprayed with a zoospore suspension of the fungus and incubated in a humidity chamber at 18°–20° C. and saturated atmospheric humidity. Wetting is discontinued after 24 hours. After the plants have dried, they are sprayed with a mixture prepared from a wettable powder formulation of the test compound in a concentration of 200 ppm. After the spray coating has dried, the plants are put back into the climatic chamber for 4 days. The number and size of the typical leaf specks occurring after this time serve as indicators for determining the efficacy of the test compounds.

b) Preventive-systemic action

A wettable powder formulation of the test compound is applied in a concentration of 600 ppm (based on the volume of the soil) to the surface of the soil of 3-week-old tomato plants of the "Roter Gnom" variety. After a waiting time of 3 weeks, the underside of the leaves of the plants is sprayed with a zoospore suspension of *Phytophthora infestans*. The plants are then kept for 5 days in a spray chamber at 18°–20° C. and saturated atmospheric humidity. The number and size of the typical leaf specks occurring after this time serve as indicators for determining the efficacy of the test compounds.

Whereas infestation is 100% on untreated and infected control plants, infestation in both tests is reduced to 20% or less with compounds of Tables 1, 2 or 3, especially with compounds 1.1, 1.3, 1.6, 1.14, 1.22 and 1.41 (0–5% infestation).

Example B2

Action against *Plasmopara viticola* (Bert. et Curt) (Berl. et DeToni) on vines a) Residual preventive action Vine cuttings of the Chasselas variety are reared in a greenhouse. Three plants in the 10-leaf stage are sprayed with a spray mixture formulation (200 ppm a.i.) of the test compound. After the spray coating has dried, the plants are infected uniformly on the underside of the leaves with a spore suspension of the fungus. The plants are then kept in a humidity chamber for 8 days, after which time marked symptoms of disease are observed on the control plants. The number and size of the infected areas on the untreated plants act as an indicator of the efficacy of the tested compounds.

b) Curative action

Vine cuttings of the Chasselas variety are reared in a greenhouse and sprayed in the 10-leaf stage on the underside of the leaves with a spore suspension of *Plasmopara viticola*. After 24 hours in the humidity chamber, the plants are sprayed with a spray mixture (200 ppm) of the test compound. The plants are then kept for another 7 days in the humidity chamber. After this time the control plants exhibit symptoms of the disease. The number and size of the infected areas on the untreated plants act as an indicator of the efficacy of the tested compounds.

Compared with the control plants, infestation on the plants treated with compounds of formula I is 20% or less. Plants treated with compounds 1.4, 1.5, 1.13, 1.41, 1.52 and 1.67 exhibit virtually no infestation.

Example B3

Action against *Pythium debaryanum* on sugarbeet (*Beta vulgaris*)

a) Action after soil application

The fungus is cultivated on sterile oat grains and added to a mixture of soil and sand. Flowerpots are filled with the infected soil in which sugarbeet seeds are then sown. Immediately after sowing, an aqueous suspension (20 ppm a.i., based on the volume of the earth) prepared from a wettable powder formulation of the test compound is poured over the soil. The pots are then stood in a greenhouse at 20°–24° C. for 2–3 weeks. The soil is kept uniformly moist by continual light spraying with water. Evaluation of the test is made by observing the emergence of the sugarbeet plants and counting the number of healthy and diseased plants.

b) Action after dressing application

The fungus is cultivated on sterile oat grains and added to a mixture of soil and sand. Flowerpots are filled with the infected soil in which sugarbeet seeds are sown that have been dressed with a dressing powder formulation of the test compound (1000 ppm a.i., based on the weight of the seeds). The pots are then stood in a greenhouse at 20°–24° C. for 2–3 weeks. The soil is kept uniformly moist by lightly spraying it with water. Evaluation of the test is made by observing the emergence of the sugarbeet plants and counting the number of healthy and diseased plants.

After treatment with compounds of formula I, more than 80% of the plants emerge. In the pots, only isolated plants of unhealthy appearance are observed.

Example B4

Residual-protective action against *Cercospora arachidicola* on groundnut plants Groundnut plants 10–15 cm in height are sprayed to drip point with an aqueous spray mixture (0.02 ppm a.i.) of the test compound and infected 48 hours later with a conidia suspension of the fungus. The infected plants are incubated for 72 hours at c. 21° C. and high humidity and then stood in a greenhouse until the typical leaf specks occur. Evaluation of the fungicidal action is made 12 days after infection and is based on the number and size of the specks.

Compounds of formula I reduce the leaf specks to below c. 10% of the leaf surface. In some cases, infestation is reduced to 0–5% (compounds 1.1, 1.3, 1.4, 1.5, 1.6, 1.9, 1.22, 1.40, 1.41, 1.52, 1.62, 1.63, 1.67).

Example B5

Action against *Puccinia graminis* on wheat a) Residual-protective action

Wheat plants are sprayed to drip point 6 days after sowing with an aqueous spray mixture (0.02% a.i.) of the test compound and infected 24 hours later with a uredospore suspension of the fungus. After an incubation time of 48 hours (conditions: 95–100% relative humidity at 20° C.), the plants are stood at 22° C. in a greenhouse. Evaluation of the rust pustule development is made 12 days after infection.

b) Systemic action

Wheat plants are drenched 5 days after sowing with an aqueous spray mixture of the test compound (0.006% a.i., based on the volume of the soil). Care is taken that the spray mixture does not come in contact with the growing parts of plants. After 48 hours, the plants are infected with a uredospore suspension of the fungus. After an incubation period of 48 hours (conditions: 95–100% relative humidity at 20° C.), the plants are stood at 22° C. in a greenhouse. Evaluation of the rust pustule development is made 12 days after infection (compounds 1.1, 1.3 and others).

Compounds of formula I, especially those of Table 1, effect a marked reduction of fungus infestation, in some eases to 10–0%: compounds 1.1, 1.3, 1.5, 1.6, 1.13, 1.28, 1.58, 1.67.

Example B6

Action against *Pyricularia oryzae* on rice plants
a) Residual-protective action After a cultivation period of 2 weeks, rice plants are sprayed to drip point with an aqueous spray mixture (0.02 ppm a.i.) of the test compound. After 48 hours the treated plants are infected with a conidia suspension of the fungus. Evaluation of fungus attack is made 5 days after infection, while maintaining conditions of 95–100% relative humidity and 22° C.

b) Systemic action 2-week-old rice plants are drenched with a spray mixture of the test compound (0.006% a.i., based on the volume of the soil), while ensuring that the spray mixture does not come in contact with the growing parts of plants. The pots are then filled with water until the lowermost parts of the rice stalks are standing in water. After 96 hours the treated rice plants are infected with a conidia suspension of the fungus. Fungus infestation is evaluated after incubating the infected plants for 5 days at 95–100% relative humidity and c. 24° C.

Compounds of formula I substantially inhibit the outbreak of the disease on the infected plants, e.g. compounds 1.4, 1.5, 1.20, 1.28, 1.52, 1.67.

Example B7

Action against *Erysiphe graminis* on barley
a) Residual protective action

Barley plants about 8 cm in height are sprayed to drip point with a spray mixture (0.02% a.i.) of the test compound and the treated plants are dusted with conidia of the fungus 3 to 4 hours later. The infected plants are stood in a greenhouse at c. 22° C. and fungus infestation is evaluated 10 days after infection.

b) Systemic action

Barley plants about 8 cm in height are drenched with an aqueous spray mixture (0.002% a.i., based on the volume of the soil) prepared from a wettable powder formulation of the test compound. Care is taken that the spray mixture does not come in contact with the growing pans of the plants. The treated plants are dusted 48 hours later with conidia of the fungus. The infected plants are then stood in a greenhouse at c. 22° C. and evaluation of infestation is made 10 days after infection.

Compounds of formula I are substantially able to reduce infestation to less than 20%, and in some cases also almost completely (compounds 1.1, 1.5, 1.12, 1.13, 1.22, 1.33, 1.58, 1.63, 1.67.

Example B8

Action against *Podosphaera leucotricha* on apple shoots
Residual-protective action Apple cuttings with c. 15 cm fresh shoots are sprayed with a spray mixture (0.06% a.i.) of the test compound. The plants are infected 24 hours later with a conidia suspension of the fungus and then stood in a humidity chamber at 70% relative humidity at 20° C. Fungus infestation is evaluated 12 days after infection.

Compounds of formula I, e.g. compounds 1.1, 1.16 or 1.28, inhibit infestation to less than 20%. Infestation of control plants is 100%.

Example B9

Action against *Botrytis cinerea* on apples
Residual-protective action

Artificially damaged apples are treated by dropping a spray mixture (0.02% a.i.) of the test compound on to the injury sites. The treated fruit is then inoculated with a spore suspension of the fungus and incubated for 1 week at high humidity and c. 20° C. The fungicidal action of the test compound is determined from the number of injury sites attacked by rot. Some of the compounds of formula I of Table 1, 2 or 3 are able to inhibit rot completely, e.g. compounds 1.28, 1.61 and 1.62.

Example B10

Action against *Helminthosporium gramineum*

Wheat grains are contaminated with a spore suspension of the fungus and left to dry. The contaminated grains are dressed with a suspension of the test compound (600 ppm a.i., based on the weight of the seeds). Two days later the grains are laid out on agar dishes and development of the fungus colonies around the grains is assessed after 4 days. Evaluation of the test compound is made by assessing the number and size of the colonies. Compounds 1.1, 1.28 and 1.4 1 effected complete inhibition.

Example B11

Action against *Colletotrichum lagenarium* on cucumbers

After a cultivation period of 2 weeks, cucumber plants are sprayed with a spray mixture (concentration: 0.002%) of the test compound. Two days later the plants are infected with a spore suspension ($1.5 \times 10^5$ spores/ml) of the fungus and incubated for 36 hours at 23° C. and high humidity. Incubation is then continued at normal humidity and c. 22°–23° C. Fungal infestation is evaluated 8 days after infection. Infestation of untreated and infected control plants is 100%.

Some of the compounds of formula I inhibit infestation almost completely, e.g. compounds 1.1, 1.5, 1.13, 1.15, 1.20, 1.22, 1.52, 1.65.

Example B12

Residual protective action against *Venturia inaequalis* on apple shoots

Apple cuttings with 10–20 cm long fresh shoots are sprayed with a spray mixture (0.006% a.i.) prepared from a wettable powder formulation of the test compound. The plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection.

Compounds of Tables 1–3 are very effective against Venturia (infestation less than 20%). Thus compounds 1.1, 1.3, 1.5, 1.13, 1.14, 1.15, 1.41, 1.52 reduce Venturia infestation to 0–5%. Venturia infestation on untreated, infected shoots is 100%.

Example B13

Action against *Rhizoctonia solani* (soil fungus on rice plants)
a) Protective-local soil application 12-day-old rice plants are drenched with a spray mixture prepared from a formulation of the test compound (20 ppm a.i.) without wetting the growing pans of the plants. A suspension of mycelium and sclerotia of *R. solani* is applied to the surface of the soil to infect the treated plants. The plants are incubated for 6 days at 27° C. (day) and 23° C. (night) and 100% relative humidity (humidity box) in a climatic chamber and then evaluation is made of the fungus infestation on the leaf sheath, leaves and stems.

b) Protective-local foliar application 12-day-old rice plants are sprayed with spray mixture prepared from a formulation of the test compound. The treated plants are infected one day later with a suspension of mycelium and sclerotia of *R. solani*. The plants are incubated for 6 days at 27° C. (day) and 23° C. (night) and 100% relative humidity (humidity box) in a climatic chamber and then evaluation is made of the fungus infestation on the leaf sheath, leaves and stems.

Compounds of Tables 1–3 exhibit good activity by inhibiting Rhizoctonia infestation. Thus compounds 1.1, 1.3, .1.4, 1.6, 1.9 und 1.28 inhibit fungus infestation to 0–5%. In contradistinction thereto, infestation is 100% on untreated and infected plants.

What is claimed is:

1. A compound of formula I

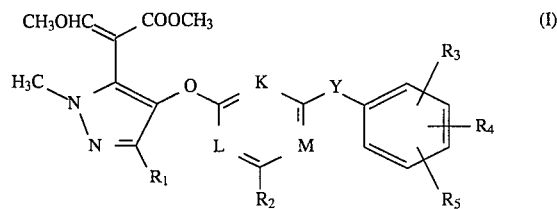

wherein $R_1$ is hydrogen or methyl, $R_2$ is hydrogen, halogen, $OCH_3$, $SCH_3$ or CN, $R_3$, $R_4$, $R_5$ are each independently of one another hydrogen, halogen, $C_1$–$C_4$alkyl, $C_1$–$C_4$alkoxy, $C_2$–$C_5$alkoxycarbonyl, $C_1$–$C_5$alkanoyl, $C_1$–$C_4$haloalkyl, $C_1$–$C_4$haloalkoxy, CN, $NO_2$, or wherein two of these substituents are adjacent to each other and together are a methylenedioxy or difluoromethylenedioxy radical, K, L, M are each nitrogen, and Y is oxygen or sulfur.

2. A compound according to claim 1, wherein $R_1$, $R_2$, K, L, M and Y have the given meanings and $R_3$, $R_4$, $R_5$ are each independently of one another hydrogen, halogen, $C_1$–$C_4$alkyl, $C_1$–$C_4$alkoxy, $C_1$–$C_4$haloalkyl, $C_1$–$C_4$haloalkoxy, CN, $NO_2$, or wherein two of these substituents are adjacent to each other and together are a methylenedioxy or difluoromethylenedioxy radical.

3. A compound according to claim 1, wherein $R_1$ is methyl, $R_4$ is hydrogen, and Y is oxygen.

4. A compound according to claim 3, wherein $R_2$ is fluoro, chloro, bromo, $OCH_3$, $SCH_3$ or CN, and $R_3$ and $R_5$ are each independently of the other hydrogen, halogen, methyl, ethyl, methoxy, ethoxy, $CF_3$, $OCF_3$, $OCHF_2$, $NO_2$ or CN, or both adjacent to each other are a methylenedioxy or difluoromethylenedioxy radical.

5. A microbicidal composition comprising as active ingredient a compound of formula I according to claim 1, together with an inert carrier.

6. A process for controlling plant diseases and for preventing infestation by microorganisms by application of a fungicidally effective amount of a compound of formula I as claimed in claim 1 to plants, to parts thereof or to the locus thereof.

* * * * *